United States Patent [19]

Fry et al.

[11] Patent Number: 5,054,470

[45] Date of Patent: Oct. 8, 1991

[54] ULTRASONIC TREATMENT TRANSDUCER WITH PRESSURIZED ACOUSTIC COUPLING

[75] Inventors: Francis J. Fry; Narendra T. Sanghvi, both of Indianapolis, Ind.

[73] Assignee: Laboratory Equipment, Corp., Mooresville, Ind.

[21] Appl. No.: 449,373

[22] Filed: Dec. 5, 1989

Related U.S. Application Data

[60] Continuation of Ser. No. 312,041, Feb. 17, 1989, which is a division of Ser. No. 163,260, Mar. 2, 1988, Pat. No. 4,951,653.

[51] Int. Cl.$^5$ ............................................. A61B 17/00
[52] U.S. Cl. .......................... 128/24 AA; 128/662.03; 128/663.01; 310/335
[58] Field of Search ........ 128/24 AA, 662.03, 663.01; 310/334–337; 73/642, 644

[56] References Cited

U.S. PATENT DOCUMENTS

| | | | |
|---|---|---|---|
| 2,913,602 | 11/1959 | Joy | 73/644 |
| 2,968,302 | 1/1961 | Fry et al. | 128/24 A |
| 3,497,728 | 2/1970 | Ostrofsky et al. | 73/644 |
| 3,636,756 | 1/1972 | White | 73/642 |
| 4,378,697 | 4/1983 | Wickramasinghe | 73/644 |

*Primary Examiner*—Lee S. Cohen
*Assistant Examiner*—Krista M. Pfaffle
*Attorney, Agent, or Firm*—Woodard, Emhardt, Naughton, Moriarty & McNett

[57] ABSTRACT

An ultrasound transducer for use with an ultrasound brain lesioning system includes an acoustic focusing lens, a piezoelectric transducer plate disposed in spaced relation with the focusing lens, an acoustic coupling medium disposed between the focusing lens and the transducer, and a pressurized fluid contacting the rear surface of the transducer to maintain a spaced relation between the transducer plate and the back surface of the lens. An electrical excitation signal is supplied to the transducer to promote production of an ultrasonic signal by the transducer.

7 Claims, 4 Drawing Sheets

ULTRASONIC TREATMENT TRANSDUCER WITH PRESSURIZED ACOUSTIC COUPLING

This application is a continuation of application Ser. No. 312,041, filed Feb. 17, 1989, now abandoned, which is a division of application Ser. No. 163,260, filed Mar. 2, 1988, now U.S. Pat. No. 4,951,653.

BACKGROUND OF THE INVENTION

The present invention relates in general to brain lesioning methods and apparata. More particularly, the present invention relates to a combination system for brain lesioning which initially uses a separate visualization system for site localization. The data from the visualization system is digitized and translated by computer into linear and rotary positioning means for positioning the ultrasound transducer which is used to create volume lesions. The separate visualization system may be a CT or MRI scan or may be ultrasonic imaging. The required output in the depicted configuration is a transparency of the imaged tumor or other volume to be lesioned which can then be translated into a computer by use of a digitizing tablet.

Traditionally, the selected method for treatment of brain tumors and related disorders was to first take and process an X-ray film of the brain and from that film roughly determine the size, shape and location of the tumor. The next step was to surgically remove as much of the tumor as possible. As technology has advanced, X-ray usage has yielded to other visualization methods, such as ultrasound, CT scan techniques and MRI utilization. The surgical procedures have expanded to cryoknives and gamma knives. Radon seeds have been implanted and ionizing radiation used. Each of these approaches has met with some success but not without their share of adverse side effects, including incomplete treatment.

Any cutting procedure is risky, especially in the area of the brain, in that the procedure may result in the incomplete removal of the tumor tissue, the excess removal of healthy tissue or both. Ionizing radiation creates a cumulative effect of the dosage to the other, surrounding brain tissue. These concerns and their attendant problems are addressed and solved by the use of ultrasound to produce volume lesions in the brain. As is well known, the noninvasive nature of ultrasound provides a safe and convenient means of treatment by selection of a suitable dosage to produce volume lesions.

The success of any ultrasound approach depends on a number of factors. Not only must the dosage (intensity and time) be controlled, but the alignment of the beam, spot size and completeness of the treatment over the full volume of the tumor or other selected tissues are critical. An added concern with the treatment of brain tumors with ultrasound is the risk of "skimming" of the ultrasound beam by the edge of the bony opening in the skull. Finally, since ultrasound is not a "sighted" treatment technique, the physician needs to have some means of determining the exact location of the tumor, its size and its shape.

The number of engineering and anatomical concerns over the use of ultrasound for treatment of brain tumors has meant that over the years there has been very little interest in producing volume lesions in the brain for the elimination of tumors. The inability to deal with these engineering and anatomical concerns has meant that a valuable treatment option has not been adequately utilized. There is no doubt that noninvasive ultrasound is preferred over the surgeon's scalpel. What has been missing and what is provided by the present invention is a means to translate the tumor location and shape determination data from a reliable imaging technique such as ultrasound, CT scan or MRI into computer-controlled linear and rotary drive means for the ultrasound transducer. By digitizing the ultrasound, CT scan or MRI data, alignment of the focused ultrasound beam can be precise and the dosage determined so as to be able to use ultrasound to produce volume lesions in the brain for the treatment of tumors. The present invention provides a number of unique and valuable structures which cooperate to provide an apparatus which is both extremely accurate and precise, and which avoids the prior art problems.

SUMMARY OF THE INVENTION

An apparatus for treatment of brain tumors or other selected brain tissues according to one embodiment of the present invention includes a skull fixation apparatus which incorporates a plurality of alignment spheres, a movable translation assembly which includes a precision ball for providing linear and rotary positioning data by way of a cup which is adapted to fit over the plurality of spheres, a linear encoder which cooperatively interfaces with the precision ball for deriving X, Y and Z linear positioning data, a pair of rotary encoders which cooperatively interface with the precision ball for deriving rotary positioning data, digitizing means for deriving skull fixation coordinates and tumor data from an image transparency produced by a suitable imaging or scan technique, computer means which cooperatively interface with the digitizing means for retrieving and storing skull fixation coordinates and tumor data from the imaging or scanner means, and wherein the computer means is operatively coupled to the linear encoder and to the pair of rotary encoders for receiving linear and rotary positioning data and which is operable to automatically move the transducer in both linear and rotary directions such that the focused beam of ultrasound from the transducer is able to be directed at the locations of the brain tumors.

A method of transforming spatial geometry into a radiation system for treatment of brain tumors according to another embodiment of the present invention comprises the steps of placing the patient into a skull fixation device, applying spatial coordinate landmarks to the skull fixation device, producing image data of the patient's skull and any brain tumor including image data of the spatial coordinate landmarks, transferring the image data and the spatial coordinate landmarks to the digitizing means, positioning the patient in an ultrasound treatment apparatus with the skull fixation device attached, modifying the skull fixation device by adding reference landmarks, coupling coordinate translating means to the reference landmarks for deriving linear and rotary coordinate positions of the reference landmarks to the skull fixation device, processing the image data and the derived coordinates of the reference landmarks into transducer movement data for directing the movement of the treatment transducer, and generating volume lesions by ultrasound into any brain tumor.

One object of the present invention is to provide an improved method and apparatus for generating volume lesions in the brain by focused ultrasound.

Related objects and advantages of the present invention will be apparent from the following description.

DESCRIPTION OF THE PREFERRED EMBODIMENT

Figure 1:
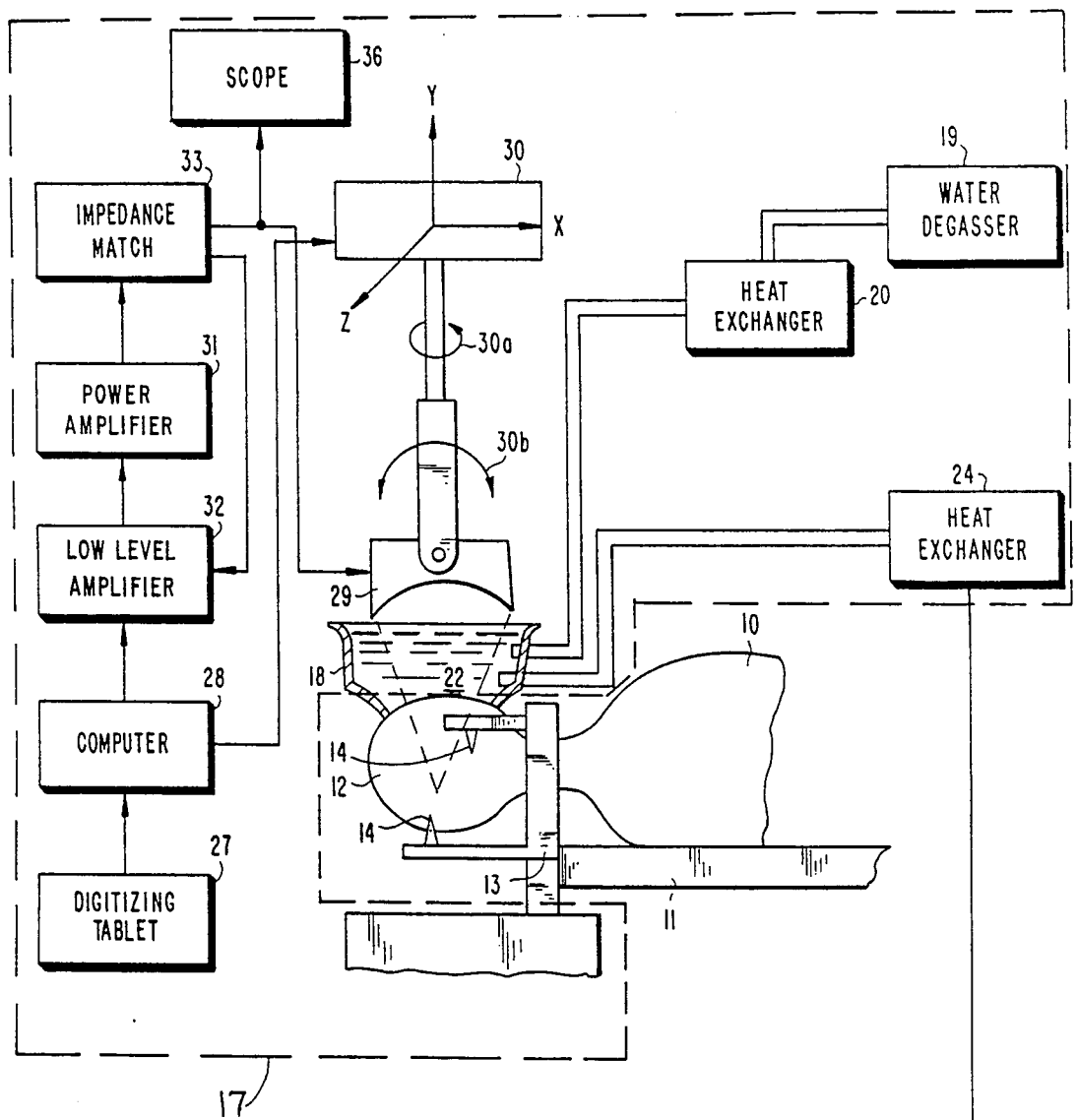
FIG. 1 is a diagrammatic illustration of the main component parts and their relationship to one another according to a typical embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1, there is a diagrammatic illustration of the main portions of the present invention. The patient 10 is shown lying on table 11. As illustrated, the patient shown is lying on his side but it should be understood that the system permits any patient position, including even a sitting position. The skull 12 is shown attached to rigid skull fixation apparatus 13. Metal pins 14 are driven into the skull 12 for rigidly fixing the skull in position as is well known in the art. Although only two pins 14 are illustrated, a third pin is employed on somewhat equal radial spacing so as to suitably support the skull.

Figure 1A:
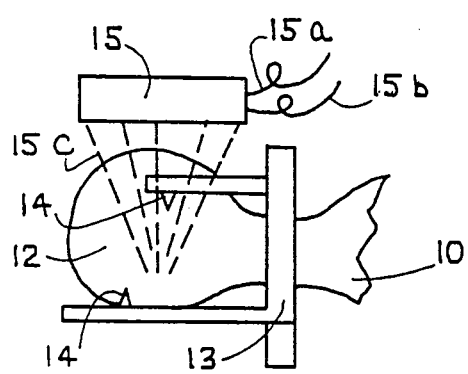
FIG. 1A is a diagrammatical illustration of the patient positioned for initial imaging.

Prior to placing the patient in position for treatment by ultrasound irradiation apparatus 17, the patient has been subjected to some form of imaging technique as shown in FIG. 1A in order to generate brain site identification and localization data which will include the size, shape and location of any tumors and landmarks which establish a precise frame of reference and orientation for the patient. Imager 15 is representative of the suitable forms of imaging for the present invention, including ultrasound, CT scan or MRI with lines 15a and 15b being representative of information transmission lines for the image data and line 15c being representative of the transmitted and/or received image signals. Regardless of the technique, external landmarks must be provided for precisely locating the skull features and tumors spatially relative to the fixation apparatus 13. The patient still with apparatus 13 attached is then placed in position for treatment by the ultrasound irradiation apparatus 17. As will be explained in greater detail hereinafter, a coordinate transformation is made from the coordinates in brain space as derived from the imaging data to brain space relative to the ultrasound irradiation apparatus for the computer controlled, automatic guiding and positioning of the ultrasound transducer it is thus important for apparatus 13 to remain fixed in position relative to the position of apparatus 17.

It is to be understood that while a number of significant advantages in the treatment of brain tumors are derived by the use of ultrasound, ultrasound is not a "sighted" technique and thus some means must be provided in order to precisely identify the location of the brain tumors or other brain sites as well as their size and geometry. Since these particular features and data can be derived from ultrasonic imaging or CT or MRI scans, one of those techniques is initially applied for subsequent use in practicing the present invention. However, simply having this data, whether in the form of transparencies or data signals derived from these scans is not sufficient unless coordinate landmarks are provided on the transparency or as part of the image data signals so that they can be used as a point or frame of reference for the ultrasound transducer. The translating of this imaging data from the scan transparency into the mechanical drive for the transducer is critical to the success of the present invention. However, if transparencies are not used, the image data signal is input directly into the computer. The referenced landmarks may take various forms but they need to have a specific, fixed and known position relative to fixation apparatus 13. The dimensional (coordinate) relationship can be programmed into the computer control to assist in position identification. Additionally, these landmarks must be visible on the image transparency, if that form of data entry is used, so that their position can be digitized and input into the computer.

Once the patient is in place, a Steridrape cloth with a hole large enough to outline the edge of the scalp area of the ultrasound or radiation field is attached to the patient's scalp. The cloth is then drawn up through an open bottom in waterbath support 18 so that this plastic liner forms a water-tight container from the surface of the scalp to the top of the waterbath support. This waterbath support is actually supported above the patient's scalp and does not rest on the scalp.

A water degasser 19 (shown as a boiling unit) provides hot, degassed water through heat exchanger 20. The water output through heat exchanger 20 is controlled to the normal body temperature as waterbath support 18 is filled with degassed water 22. Heat exchanger 24 provides circulating water through coils and waterbath support 18 in order to maintain a fixed temperature for the degassed water 22. It should also be noted that the patient as illustrated has a lateral skull section removed which is done surgically at a previous time and the ultrasound irradiation is conducted through the hole in the scalp.

The generated transparencies, which will be the form of data entry described for the preferred embodiment, from either the ultrasonic imaging or by CT or MRI scans (and which include reference landmarks or benchmarks) are placed on digitizing tablet 27 which is back-illuminated. The digitizing tablet with either a light pen or similar data pick up and transferring means, such as a cursor, enables the physician or technician to locate the reference landmarks and to outline the various tumor areas. Also digitized is the opening in the skull so that its geometric center can be established. As should be well known by those of ordinary skill in the art, with a CT scan a plurality of transparencies are taken due to the multiple "slices" through the brain which must be derived in order to provide, volume information. Thus, this digitizing step must be repeated for all the CT transparencies for the particular patient such that when completed, there is total geometry data of the entirety of all tumors or other brain sites and those tumors are positioned relative to the referenced landmarks. All essential features of the brain sites, skull opening, reference landmarks are scanned on digitizing tablet 27 and all of this information is stored in computer 28.

From the transparencies which are outlined and transferred from digitizing tablet 27 to computer 28, all of the dimensional information is provided to the formulation for computing the voltage drive levels to all sites in order to give the necessary sound intensity at the selected brain sites. Since the brain volume selected for ablation is in general of a complex shape, this complexity is treated by a multiplicity of individual ultrasound lesions. The focal position for each of these individual ablation sites is selected by the computer 28 through preprogramming, and the transducer focus is automatically brought to the appropriate sites. The transducer 29 is provided with five degrees of freedom. There are three orthogonal motions through a normal XYZ coordinate system 30 and two rotational motions as illustrated by the arrows of rotation 30a and 30b.

The programming of computer 28 has been arranged so that for each individually selected lesion site, the central ray of the ultrasonic beam from transducer 29 passes generally through the geometric center of the skull opening so that beam "skimming" at the skull bone edge is avoided.

Power is provided to the transducer 29 from power amplifier 31. Amplifier 31 is driven by a low-level amplifier 32 with its frequency source. Impedance matching network 33 couples the amplifier 31 to transducer 29. Once the required acoustic output from transducer 29 is decided, the driving voltage to transducer 29 is computed by way of computer 28 which in turn sets the input in amplifier 32 so that the required voltage is set. Once set, the feedback loop from matching network 33 to amplifier 32 maintains this fixed voltage level. As an additional check on the voltage drive level to transducer 29, an additional absolute voltage readout is provided through oscilloscope 36.

Periodic monitoring of the sound output from transducer 29 is provided by the radiation force method. A bifilar suspension 37 mounted to tank 38 by support 39 suspends a stainless steel ball 40 in a temperature controlled and degassed volume of water 43 which is contained within tank 38. This water temperature is maintained by heat exchanger 24. The transducer 29 is brought into tank 38 by placing tank 38 in apparatus 17 (without the patient in place). Coordinate system 30 (XYZ coordinates of linear motion) is a mechanical drive structure which is capable of moving transducer 29 so that the focal position of the generated ultrasound beam from transducer 29 impinges on the stainless steel ball 40.

Sound-absorbing material 44 which is mounted in tank 38 serves to suppress standing waves in tank 38 during the calibration procedure. Deflection of the stainless steel ball for a specified set of drive voltages into transducer 29 is recorded by the use of an optical telescope 45. Telescope 45 is mounted outside but attached to tank 38. Horizontal motion displacement of the stainless steel ball is recorded on micrometer 46.

This ball deflection is directly related to the sound output intensity at the focal position in the sound field and this particular method is believed to be a primary standard for measuring sound field intensity.

Figure 2:
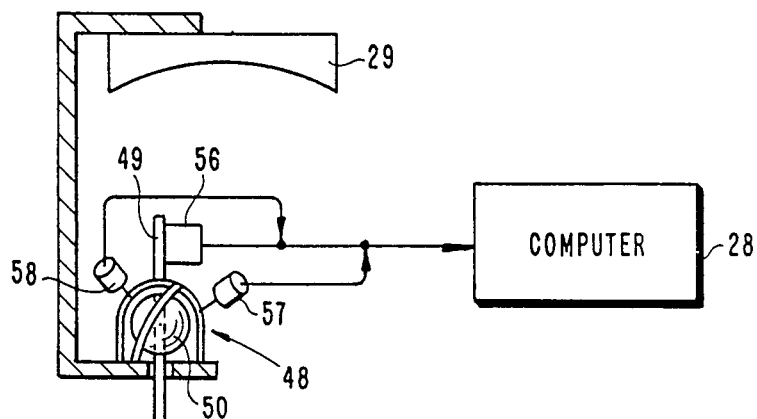
FIG. 2 is a diagrammatic illustration of positional data translating means comprising a portion of the present invention.
Figure 2A:
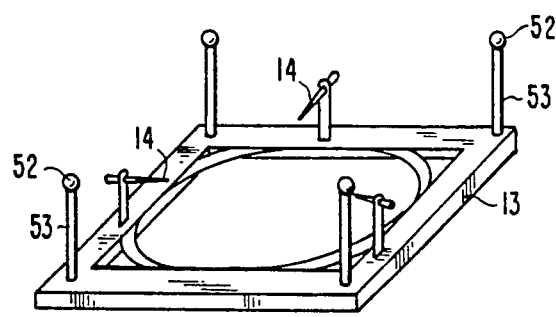
FIG. 2A is a perspective view of a skull fixation device with reference landmarks attached for spatial coordinates.

Referring to FIGS. 2 and 2A, the apparatus for transformation of coordinates to the irradiation apparatus is illustrated. This transformation is accomplished by the use of a precision joystick apparatus 48 which is attached to the back of the housing for focusing transducer 29. This joystick apparatus includes member 49 which can be linearly translated by way of precision ball 50. Universal angular motion of member 49 is provided directly through precision ball 50. Attached to member 49 is cup 51 which includes a hemispherical concave surface that is designed and sized to fit precisely over each of the balls 52 (see FIG. 2A) which are added to and supported on skull fixation apparatus 13 by corresponding upright members 53. Each combination of member 53 and ball 52 is detachable but fits into precision holes which are bored into apparatus 13. As is appropriate for complete alignment, three ball and member combinations are added to skull fixation apparatus 13. The use of these three assemblies and the interlocking of each with cup 51 permits the complete transformation of coordinates into computer 28.

The patient is positioned within apparatus 13 and the alignment balls 52 are attached. Further apparatus 13 is rigidly affixed relative to the position of apparatus 17 at a known position such that as the cup 51 is moved into position over each ball 52, the position coordinates are derived relative to apparatus 17. As should be understood, each component used in this procedure has specific dimensions and points of attachment, all of which are known and programmed into the computer. The extrapolation is sequential, but not complicated. The free space coordinates of the alignment balls is derived relative to the movement of transducer 29. These balls have a fixed position (known) relative to fixation apparatus 13 and the fixation apparatus has a fixed position (known) relative to the brain tumor(s).

It should be noted that member 49 electrically interfaces with linear encoder (potentiometers) 56 and two rotary encoders 57 and 58, which are used to obtain rotation degrees. The two rotary encoders are positioned at right angles to each other. The coordinate translating system of FIGS. 2 and 2A builds upon the image data and landmarks previously digitized. This earlier derived information provides dimensional data and space coordinates regarding the size and shape of the brain tumor(s) and their location relative to the skull fixation apparatus 13. What is missing is the positional data of the ultrasound irradiation apparatus 17 relative to apparatus 13. Once the ball 52 and member 53 assemblies are installed into their precise locations on the fixation apparatus these become the frame of reference for the transducer positioning.

The X, Y and Z coordinates and the two degrees of rotary freedom for the transducer at each position when the cup 51 is placed over each ball 52, once input into the computer, enables the transducer to be moved by computer control to each tumor position for volume lesioning. A key point to be noted is that no precise alignment is required in using this system. All that needs to be done is to position cup 51 in the proximity of each ball 52 so that the cup can be drawn over each ball for establishing the coordinates. This sequence of steps is repeated for a total of three sets of data for the complete transformation and while the system is extremely precise, it does not require any precise alignment.

Figure 3:
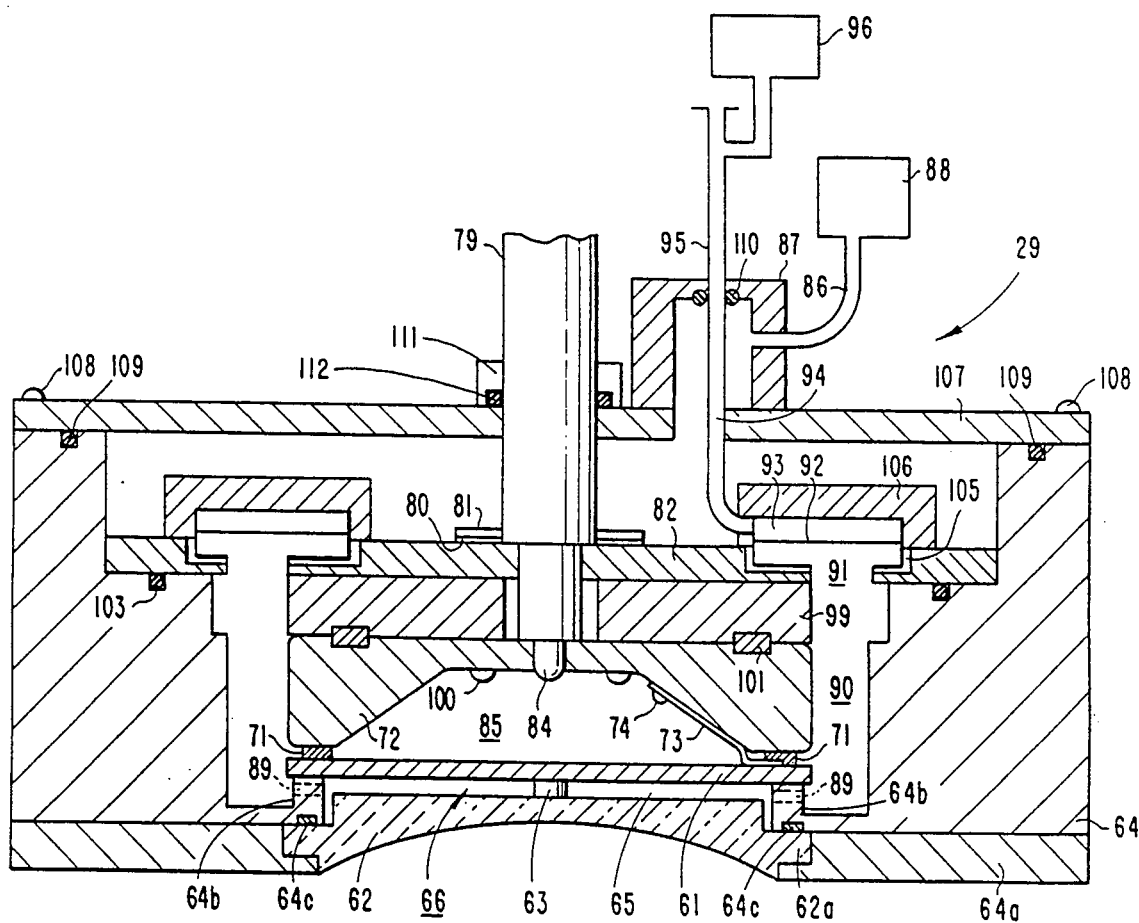
FIG. 3 is a front elevation, diagrammatic illustration in full section of the transducer design comprising a portion of the present invention.

Referring to FIG. 3, transducer 29 is illustrated in greater detail including several unique features which are provided in order for a stable acoustic output to be obtained at all preselected driving levels. These driving levels are required in order to produce controlled focal brain lesions in deep brain sites. In order to achieve this necessary objective, it is necessary to have a stable sound-producing source such as generally circular (disc) quartz plate 61 which is used in this particular embodiment. The quartz plate 61 is able to be maintained flat and parallel to generally circular, plano-concave lens 62 by the structure which will be described hereinafter. Lens 62 is a hard anodized aluminum lens with an elliptic concave surface for minimizing the half-intensity length of the beam at the focus. In order to maintain flatness and parallelism of plate 61 and lens 62 with a fixed spacing distance therebetween, the aluminum flat side of the lens is precisely machined flat with at least one ⅛-inch diameter rod 63 machined on the surface to extend a distance above the lens surface equal to a ¼ wave length in the silicone oil 65 in space 66. A suitable silicone oil for this application is Dow Corning 710 fluid.

In order to maintain this ¼ wave length spacing to within plus or minus 0.0001 inches, it is required that the outer peripheral lip 62a of aluminum lens 62 provide unanodized surfaces (flat top and bottom surfaces and outer edge surface) which rest directly in contact with the flat machined surface of housing 64 and end plate 64a. Housing 64 includes an inwardly and upwardly directed lip 64b, of an annular ring configuration, whose underside abuts against the top surface of lip 62a and whose top surface supports plate 61. The height of this lip is precisely machined since it is the means to fix the ¼ wave length separation between the plate 61 and lens 62. Rod 63 provides center stabilizing for the plate due to its span between peripheral edge supports and the pressure differential between the top and bottom surfaces of the quartz plate. The space 66 between the plate 61 and lens 62 (the ¼ wave length spacing) is filled with silicone oil 65 which is freely exchanged through radially open channels in lip 64b. Gasket 64c seals the oil in space 66.

One gold-plated and polished electrode (not shown) is electrically connected to quartz plate 61 and rests in direct contact with the top machined surface of lip 64b and provides the electrical ground contact for the quartz plate.

In order to keep plate 61 in pressure contact with housing 64, a flat, flexible compression gasket 71 is firmly pressed against plate 61 through metal member 72. In order to provide electrical contact for power to plate 61 another foil electrode 73 fabricated of an approximate 0.001 inches thick soft metal foil (gold, brass, silver) extends part-way under compression gasket 71, while the remainder of gasket 71 acts as a seal for the silicone oil. The power electrode and ground electrode (not shown) on plate 61 do not extend to the edge of plate 61 and the silicone oil provides insulation around the edge. The foil electrode 73 is attached to metal member 72 with a series of metal screws 74.

To provide RF power to drive quartz plate 61 a coaxial cable 79, with a metal outer jacket 80 is used. Jacket 80 is cut and peeled back so as to place the cut, free end of jacket 80 between plates 81 and 82. Plates 81 and 82 are clamped together using mechanical fasteners in order to establish an electrical ground on jacket 80. The coaxial cable has an end plug 84 which side pressure contacts plate (metal member) 72 through a central hole. Space 85 is an air space so that the quartz plate 61 is not back acoustically loaded thereby directing all its acoustic output through the interspace 66 and lens 62 into the oil which is in front of lens 62. To insure flatness of quartz plate 61 and parallelism with the flat surface of lens 62, the air space 85 and all other air spaces in the transducer housing 64 are pressurized through tube 86 into cover 87. This air pressure holds quartz plate 61 against machined rod 63 to maintain the necessary parallelism. Pressure is applied from source 88.

In order to maintain a positive differential pressure in space 85 relative to the pressure in interspace 66, flow communication is provided from interspace 66 via flow access channels 89 into column 90 and well 91. These areas are all silicone oil filled and in pressure equilibrium is a thin flexible diaphragm 92 which covers well 91. Above diaphragm 92, the air space 93 is exhausted through flexible tubing 94 and rigid tube 95 to the outside atmosphere.

A further feature to suppress cavitation in the oil in space 65 between the quartz plate 61 and lens 62 when the system is run at the highest acoustic output power is provided by pressure system 96 providing greater-than-atmospheric pressure to space 93. Typically this pressure will be that which prevents any cavitation in space 65 (of the order of 40–50 pounds per square inch). This pressure in space 93 is readily transmitted through diaphragm 92 to the silicone oil 65 in well 91 and hence through column 90 into space 66. The pressure provided by source 88 is in the order of 2 pounds per square inch higher than the pressure in system 96 in order to keep plate 61 flat and held against lens 62 through rod 63.

Element 99 in the transducer assembly is an insulating member to which plate 72 is bolted by screw(s) 100. Gasket 101 keeps the silicone oil contained in column 90 from reaching the coaxial cable 79. Metal plate 82 is bolted to housing 64 around the outer periphery of plate 82. Oil is kept in column 90 and well 91 by the use of O-ring seal 103 positioned between housing 64 and plate 82 and by gasket 105. Member 106 is bolted and sealed to plate 82. Top metal plate 107 is bolted by screws 108 to housing 64 and sealed thereto through O-rings 109. Metal tube 95 is sealed to cover 87 through seal 110. The coaxial cable 79 is water-tight and sealed to top plate 107 through retainer 111 and O-ring 112.

In order to accomplish the task of producing lesions of any complex size or shape in the human brain with intense focused ultrasound it is necessary to provide for ultrasound dosage conditions which produce individual focal lesions (from which the complex volume can be generated), which do not compromise brain tissue outside the intended focal lesions site and permit subsequent individual focal lesions in a contiguous manner. To do this in both gray and white matter and abnormal brain tissue, it is necessary to inhibit the production of microbubble formation at the primary focal site so that there can be no vascular dispersion of such microbubbles away from the primary focal site which microbubbles could initiate off primary site lesion production and hemorrhage due to ultrasound passage through tissue containing microbubbles.

In order to accomplish this task while being able to accomplish primary site lesions, it is necessary to derive these sound intensities as a function of frequency which will not produce microbubbles at the primary lesion site. This requires that for a 1 MHz sound frequency (a frequency necessary to achieve deep penetration into the human brain), the primary site sound intensity must not exceed 300 watts per square centimeter. At this intensity and for lower intensities, gray and white matter lesions on a multiplicity of individual contiguous sites can be produced without undesirable side effects (microbubbles). As the frequency is increased above 1 MHz, the primary site sound intensity can be increased and produce no microbubbles but the penetration capability in brain tissue returns as the sound frequency is increased. At 4 MHz frequency which is the upper frequency which can be considered for more superficial brain lesion production, the intensity which will not lead to microbubble formation is at least 2100 watts per square centimeter. At these intensity limits, the time-on period of sound irradiation at each individual site can be extended to as many seconds as is needed to ablate the tissue at the focal site without microbubble formation.

In order to constrict the individual lesion sites so that the boundaries of desired volume lesions can be constrained, the transducer configuration used will give a half intensity length at the lesion focal region in the order of 15 mm at 1 MHz operating frequency. This length of half intensity is consistent with the necessity of constraining lesions in the human brain so that the extending of individual lesions into white matter (white matter is more sensitive than gray matter) can also be constrained.

Figure 4:
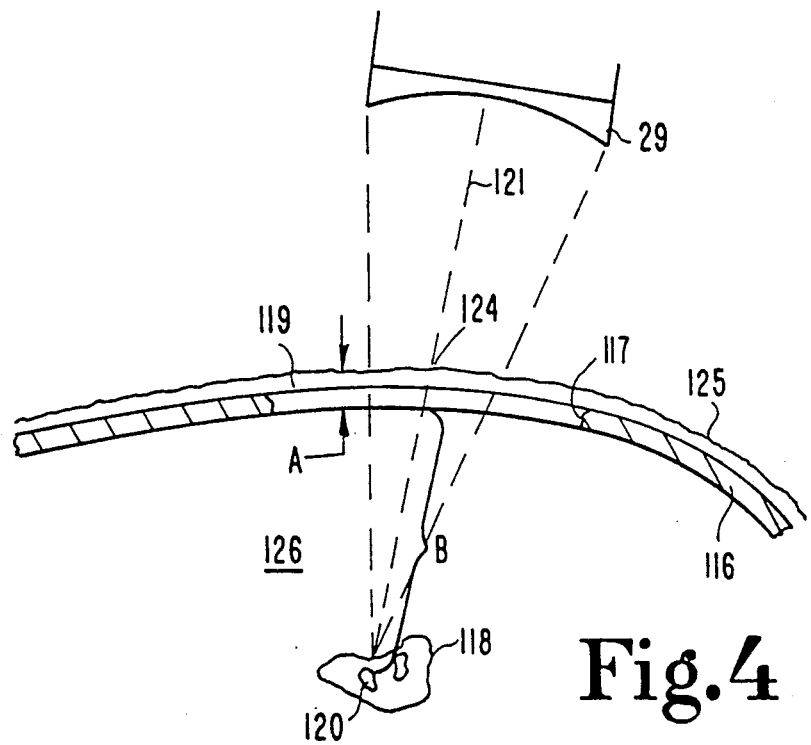
FIG. 4 is a diagrammatic illustration of the focused ultrasound beam as directed into the brain tumor.
Figure 5:
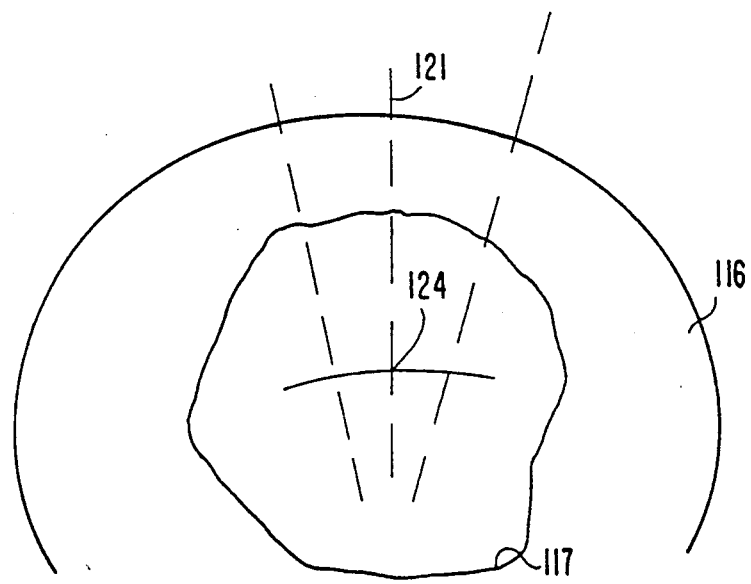
FIG. 5 is a diagrammatic illustration of the skull opening and centralizing of the ultrasound beam which is directed by the present invention.

Referring to FIGS. 4 and 5, the details of the ultrasound being focused and central beam axis are shown with respect to the skull bone opening, the brain volume site to be lesioned and the tissue depth which is described in order to compute the tissue attenuation from the scalp surface to the brain volume selected to be lesioned.

Skull 116 with skull hole outline 117 is constructed (digitized) in computer 28 along with brain tissue volume 118 and scalp and muscle tissue 119. Prior information on individual brain lesion 120 dimensions along with preselection of the pattern in which the individual lesions 120 are to be produced, spacing of individual lesions to give the desired overlap in tissue boundary patterns are processed in the computer. Individual lesions 120 within volume 118 are irradiated along the central axis 121 of the beam with the axis programmed to pass through the skull opening 117 at the geometric center 124. As the transducer changes orientation by computer control, the central axis will shift, but the focal point of the beam will be at the desired lesion site and the central axis will be close to the center 124.

Each individual lesion 120 within volume 118 has its distance computed along the transducer beam axis starting at the scalp surface 125, proceeding through the scalp and muscle 119 (distance A) through the brain tissue 126 (distance B). The scalp and muscle average attenuation coefficient and the brain attenuation coefficient along with dimensions A and B are involved in the computation of total acoustic beam loss. From these computations, the necessary driving voltage to transducer 29 is provided automatically for each individual lesion site 120 in brain tissue volume 118.

It is also possible in some cases to apply the above system and technique to the production of focal lesions in the brain through the intact scalp muscle and skull bone. In this circumstance, the attenuation factor for the skull must be entered as an additional attenuation and the central beam axis of transducer 29 held within plus or minus five degrees perpendicular to the skull surface on its path to each individual lesion site 120. Although this system is specifically designed for the brain, it can be used in the transcutaneous mode to produce lesions and other appropriate body tissues.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An ultrasound treatment transducer assembly for directing a focused ultrasound beam at an anatomical site, said transducer assembly comprising:
   an acoustic focusing lens having a concave front surface and a substantially flat back surface;
   a substantially flat piezoelectric transducer plate disposed in spaced relation to said focusing lens and having a rear surface and a front surface which is disposed at a fixed distance of separation with respect to the back surface of said acoustic focusing lens;
   an acoustic coupling medium disposed between the back surface of said focusing lens and the front surface of said transducer plate;
   first pressurizing means contacting said acoustic coupling medium for maintaining said acoustic coupling medium between said transducer plate and said focusing lens at a desired pressure; and
   air pressure means contacting the rear surface of said transducer plate for applying air pressure against said rear surface, wherein the pressure applied against said rear surface by said air pressure means is higher than the desired pressure on the front surface of said transducer plate due to said acoustic coupling medium to maintain the spaced relation between said front surface of said transducer plate and said back surface of said lens.

2. The ultrasound treatment transducer assembly of claim 1 further comprising a flexible diaphragm wherein said first pressurizing means includes an enclosed volume filled with said acoustic coupling medium and a source of air pressure, said enclosed volume and said source of air pressure being separated by said flexible diaphragm.

3. The ultrasound treatment transducer assembly of claim 2 wherein said acoustic coupling medium is silicone oil.

4. The ultrasound treatment transducer assembly of claim 3 which further includes a spacer positioned between and in contact with the front surface of said transducer plate and the back surface of said focusing lens.

5. The ultrasound treatment transducer assembly of claim 4 wherein the distance of separation of said transducer plate front surface and said focusing lens back surface is established by said spacer and is equal to approximately one-fourth wavelength of the ultrasound beam in said silicone oil.

6. The ultrasound treatment transducer assembly of claim 1 wherein said acoustic coupling medium is silicone oil.

7. The ultrasound treatment transducer assembly of claim 1 further comprising a spacer wherein the distance of separation of said transducer plate front surface and said focusing lens back surface is established by said spacer and is equal to approximately one-fourth wavelength of the ultrasound beam in said silicone oil.

* * * * *